United States Patent [19]
Burguiere et al.

[11] Patent Number: 5,846,566
[45] Date of Patent: Dec. 8, 1998

[54] MICROCAPSULES FOR THE CONTROLLED RELEASE OF ACETYLSALICYLIC ACID IN THE GASTROINTESTINAL ENVIRONMENT

[75] Inventors: Olga Burguiere, Castelnau le Lez, France; Ahmad Yassine, Borj-Barajne, Lebanon; Jean-Philippe Selles, Montpellier, France

[73] Assignee: Flamel Technologies, Venissieux Cedex, France

[21] Appl. No.: 753,013

[22] Filed: Nov. 19, 1996

Related U.S. Application Data

[62] Division of Ser. No. 227,122, Apr. 13, 1994, Pat. No. 5,603,957.

[30] Foreign Application Priority Data

Apr. 19, 1993 [FR] France ................................ 93-04560

[51] Int. Cl.⁶ .................................................. A61K 9/14
[52] U.S. Cl. ..................... 424/489; 424/490; 424/470; 424/458
[58] Field of Search ................... 424/489, 490, 424/458, 470

[56] References Cited

U.S. PATENT DOCUMENTS

| | | | |
|---|---|---|---|
| 3,892,769 | 7/1975 | Shen et al. | 260/326.13 |
| 4,308,251 | 12/1981 | Dunn et al. | 424/19 |
| 4,693,896 | 9/1987 | Wheatley et al. | 424/480 |
| 5,158,636 | 10/1992 | Groitzch et al. | 521/63 |
| 5,206,030 | 4/1993 | Wheatley et al. | 424/490 |
| 5,248,516 | 9/1993 | Wheatley et al. | 427/2.14 |
| 5,409,711 | 4/1995 | Mapelli et al. | 424/490 |
| 5,603,957 | 2/1997 | Burguiere et al. | 424/489 |

FOREIGN PATENT DOCUMENTS

| | | |
|---|---|---|
| A-0 207 041 | 12/1986 | European Pat. Off. . |
| A-0 411 590 | 2/1991 | European Pat. Off. . |
| A-0 413 120 | 2/1991 | European Pat. Off. . |

*Primary Examiner*—Thurman K. Page
*Assistant Examiner*—William E. Benston, Jr.
*Attorney, Agent, or Firm*—Bacon & Thomas

[57] ABSTRACT

The present invention relates to controlled-release microcapsules of acetylsalicylic acid which comprise particles of acetylsalicylic acid with a size of between 100 and 1000 $\mu$m, coated with a coating material consisting of a mixture of a cellulosic film-forming polymeric derivative, an antiadherent, a plasticizer, a lubricant and a vinylic film-forming polymeric derivative. The invention further relates to a process for the preparation of said microcapsules.

24 Claims, 11 Drawing Sheets

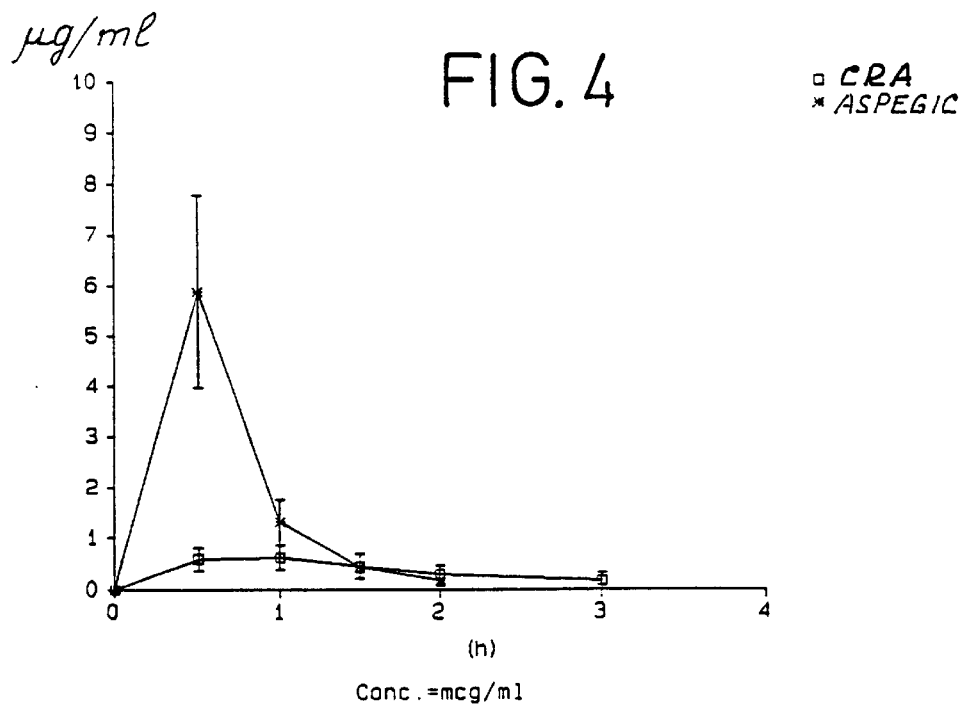
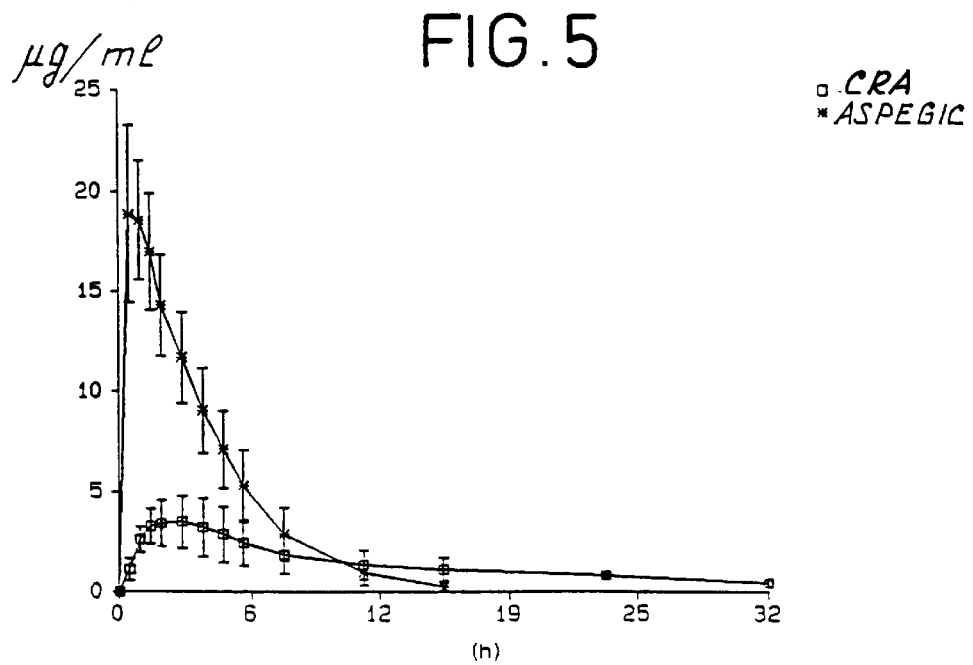

FIG. 7
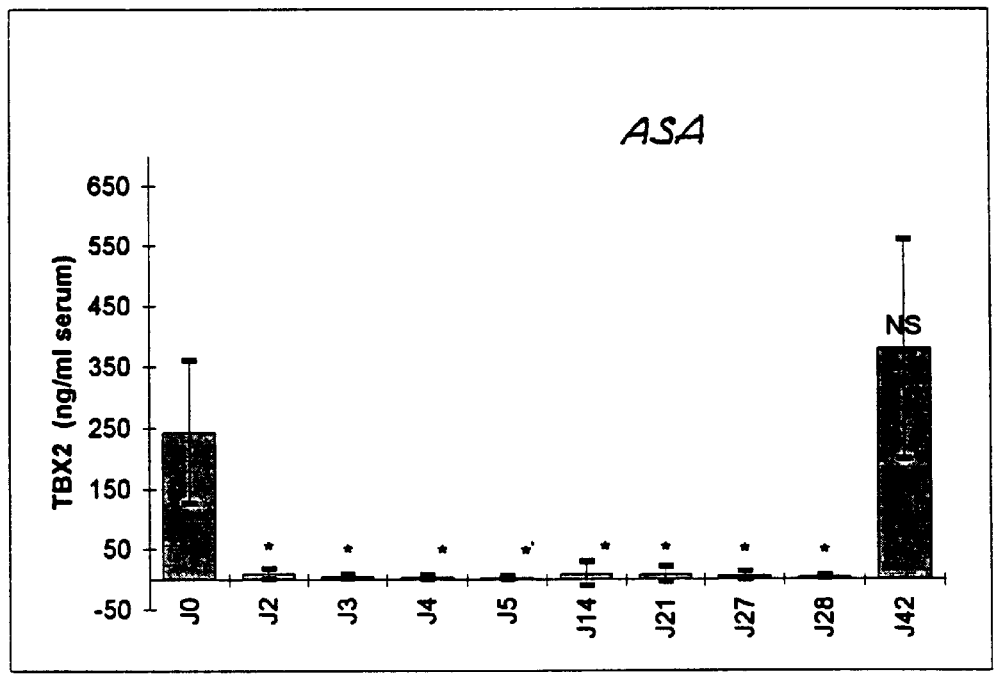
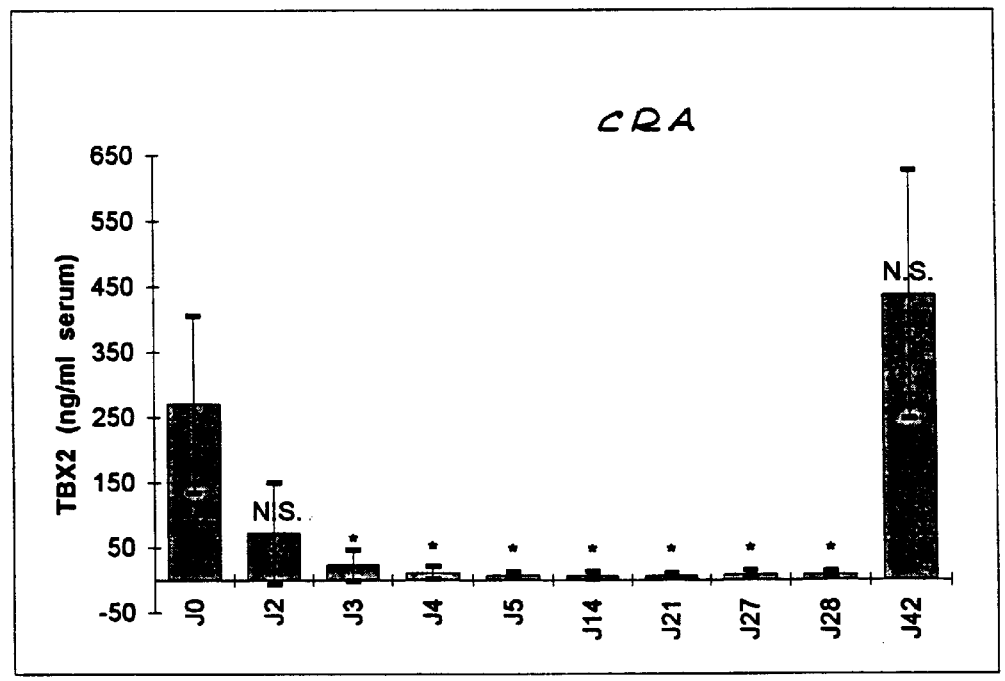
FIG. 8

FIG.13
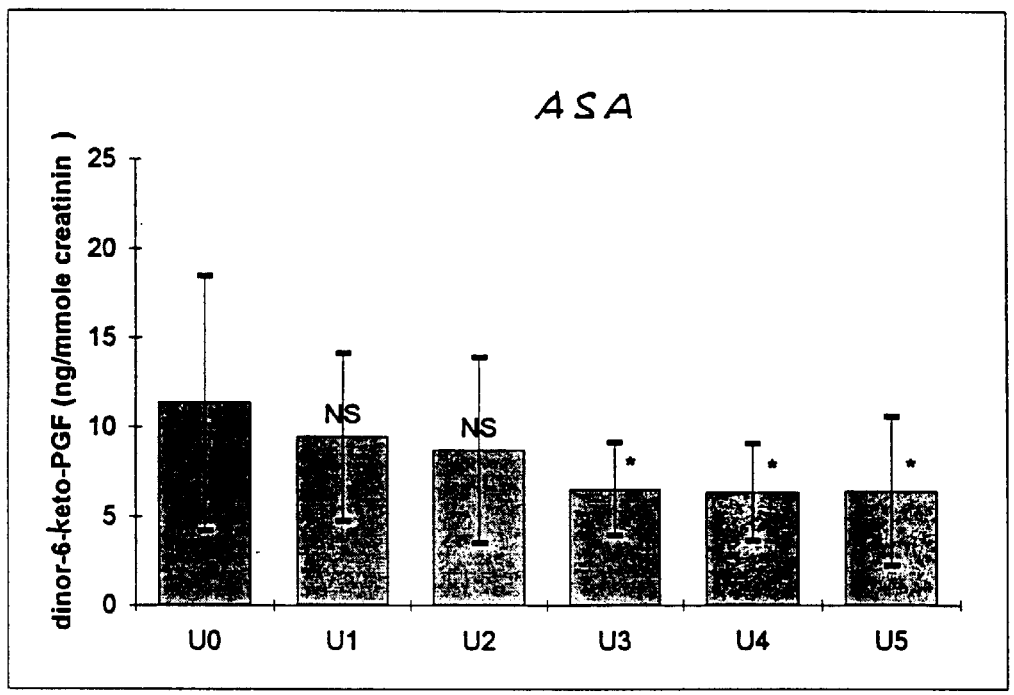
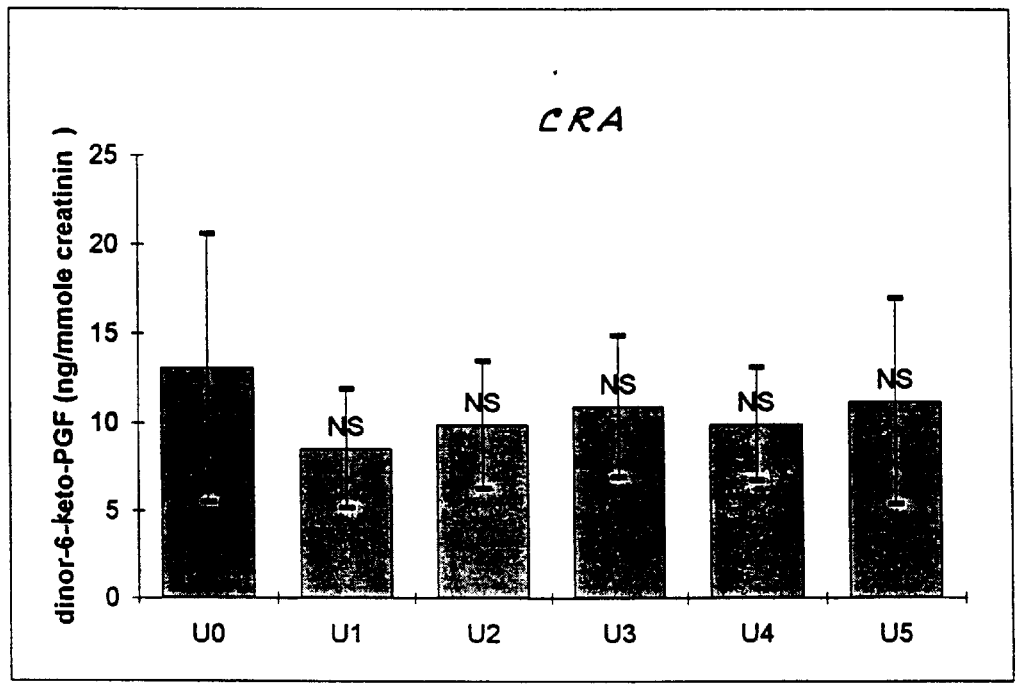
FIG.14

MICROCAPSULES FOR THE CONTROLLED RELEASE OF ACETYLSALICYLIC ACID IN THE GASTROINTESTINAL ENVIRONMENT

This application is a division of application Ser. No. 08/227,122, filed Apr. 13, 1994, now U.S. Pat. No. 5,603,957.

The invention relates to microcapsules for the controlled release of acetylsalicylic acid in the gastrointestinal environment. Controlled release of acetylsalicylic acid is understood as meaning that the kinetics of this release are controlled throughout the length of the gastrointestinal tract.

The invention further relates to a process for the preparation of the above microcapsules.

The pharmaceutical objectives of the invention are especially the selective inhibition of the cyclooxygenase specific for the production of thromboxane, to the exclusion of the other prostaglandins (prostacycline) making it possible to optimize the inhibition of platelet aggregation, in order to prevent and/or treat cardiovascular diseases and risks.

The commercial name "aspirin" or the abbreviation "ASA" will be used hereafter to denote acetylsalicylic acid.

The research and development of novel controlled-release forms have been the subject of constant interest in the pharmaceutical industry for many years. In fact, in general terms, controlling the kinetics of release of an active principle makes it possible to maintain the latter at a stable plasma level for a desired length of time, while at the same time reducing the side-effects associated with a sudden and massive release of this active principle.

Controlled-release forms are particularly advantageous in the case of certain active principles such as aspirin, insofar as they offer not only the advantages which have just been described, but also the advantage of permitting a better local tolerance and that of modifying the pharmacological and pharmacokinetic properties of these active principles.

As far as aspirin is concerned, its uses as an analgesic, antipyretic and antiinflammatory are well known. The properties of aspirin as a platelet aggregation inhibitor have been demonstrated more recently. Aspirin acts on platelet aggregation by inhibiting the cyclooxygenase which catalyzes the conversion of arachidonic acid to thromboxane in the platelets, thromboxane being a potent vasoconstrictor and a platelet aggregation stimulator.

The inhibition of the platelet cyclooxygenase is the result of its acetylation by aspirin. This acetylation takes place in the liver during the first passage through the liver.

This mechanism can rapidly reach saturation, however, and aspirin which has not been deacetylated in the liver passes into the general circulation and causes the acetylation of the cyclooxygenase in the other cells, especially those of the vascular and gastric endothelium.

Now, the cyclooxygenase of the vascular and gastric endothelium catalyzes the formation of prostacycline, which, contrary to thromboxane, is a vasodilator, a platelet aggregation inhibitor and a cytoprotector. Inhibiting the vascular and gastric cyclooxygenase therefore results in inhibition of the prostacycline and other prostaglandins (PGE), which not only runs counter to the desired effect on platelet aggregation, but also causes side-effects of aspirin on the gastrointestinal mucosa. This phenomenon of blind inhibition of the different prostaglandins in the organism is commonly referred to as the dilemma of aspirin. It is well known to scientists and has been widely described in the literature.

It is therefore of prime importance to promote the direct action of aspirin on the blood platelets in the portal circulation, but on the other hand to minimize its effect on the cyclooxygenases of the vessel walls by minimizing the amount of aspirin in the systemic circulation.

The formulations known hitherto, for example those described in FR-A-2 539 995, do not make it possible to achieve such a result, the aspirin being released too rapidly.

Patent application FR-A-2 539 995 describes microgranules containing aspirin which are designed to improve its gastric tolerance and to increase the duration of drug impregnation. These microgranules are formulated to release the whole of their active principle in the duodenal environment within 4 hours.

The aspirin is bound to carrier particles of about 500 to 600 $\mu$m in diameter by means of successive coating operations: a layer of aspirin in a mixture of polyvidone excipient and ethyl phthalate and a layer of anionic methacrylic acid polymer until the desired release kinetics are obtained.

The galenical forms described in FR-A-2 539 995, which release 100% of the active principle in 4 hours, are suitable for the normal uses of aspirin (analgesic, antipyretic, antiinflammatory), but not for its administration as a platelet aggregation inhibitor.

The well-known dilemma of aspirin referred to above was first recognized in patent application EP 0 411 590. Faced with this dilemma, the invention proposed in said patent application consists of a pharmaceutical preparation for inhibiting platelet aggregation which consists of microcapsules comprising an inner core of ASA covered with a layer of coating agent (e.g. an acrylic/methacrylic copolymer), which is itself covered with an outer layer of aspirin. With this preparation, the absorption of ASA takes place in two successive pulses of 80–120 mg and 180–220 mg of ASA.

Said patent application gives no experimental facts showing the efficacy of the preparation in resolving the dilemma:

inhibition of the thromboxane, sparing of the prostacycline and other prostaglandins, gastric tolerance.

The amounts of ASA released with each pulse are still too large over too short a time and saturate the hepatic aspirin deacetylation system.

Another proposal of the prior art, relating to galenical forms of aspirin which inhibit the thromboxane without reducing the level of circulating prostacycline, is described in patent application EP 0 377 439. These galenical forms are granules of aspirin coated with a coating composition comprising an acrylate/methacrylate copolymer, hydroxypropyl cellulose and sodium chloride. The coating agent thus produced represents 10 to 35% by dry weight of the granules. These galenical forms provide release kinetics of 5 to 15 mg/hour for periods of 8 hours at doses of 40 mg to 120 mg.

All in all, the invention described in said patent application EP 0 377 439 logically proposes to mitigate the dilemma of aspirin by reducing the doses of ASA for a release period limited to 8 hours. This is insufficient since it provides therapeutic cover for only a third of the time necessary for total inhibition of the thromboxane over 24 hours.

These galenical forms, presented as useful in the treatment of vascular occlusive complaints in man, are not satisfactory. In fact, the results obtained in an important study on healthy volunteers show that the inhibition of the serum thromboxane is 85% with a form containing 50 mg of active principle and 90% with a form containing 75 mg of active principle, the placebo itself giving an inhibition of about 10%. Measurement of the urinary thromboxane gives inhibition values of 60 and 70% respectively.

Now, to be pharmacologically effective on platelet aggregation, the thromboxane inhibition must be greater than 95%. Furthermore, a thromboxane inhibition of 100% may not be sufficient to prevent platelet aggregation induced by the collagen and the adenosine diphosphate. Finally, the daily regeneration of the platelets (⅙ to ⅒ of the initial quantity in healthy subjects, ¼ in subjects at risk) and the production of thromboxane for rapid regeneration by the megakaryocytes leaves individuals who take a daily dose of conventional aspirin very substantially below the minimum percentage of thromboxane inhibition (95%); in addition, it is impossible to correct the aggregating effect by the presence of aggregation-inhibiting vascular prostacycline, which itself is inhibited to the extent of 25%. The galenical forms according to patent application EP 0 377 439 do not therefore resolve the dilemma of aspirin.

Moreover, they are not suitable for preventing mycocardial infarctions. In fact, the frequency of such cardiac diseases increases between 4 and 8 am and between 6 and 10 pm. This phenomenon is attributable to hyperaggregation in the morning and evening. It is therefore of prime importance to have ASA in the portal vein throughout the nycthemeron so that the thromboxane is inhibited; this cannot be achieved with the galenical forms described in patent application EP 0 377 439.

In such a state of the art, one of the essential objectives of the invention is to provide a galenical form based on ASA which:

is active especially as a platelet aggregation inhibitor over 24 hours so as to necessitate only one dose a day to ensure total therapeutic cover for 24 hours, which also makes it possible to lower the total cost of the treatment, provides a satisfactory solution to the dilemma of aspirin through its biochemical selectivity towards thromboxane in order to achieve maximum therapeutic efficacy, is perfectly tolerated by the organism, and can be prepared industrially by a simple, rapid and economic process.

BRIEF DESCRIPTION OF DRAWINGS

FIGS. 4 and 5 show the change in the mean plasma concentrations in micrograms/ml of ASA and SA, respectively, as a function of time.

FIGS. 7 and 8 show the inhibition of thromboxane $B_2$.

FIGS. 13 and 14 demonstrate the effect of the control ASA and the encapsulated ASA on the inhibition of urinary dinor-6-ketoprostaglandin F1 α.

Figure 1:
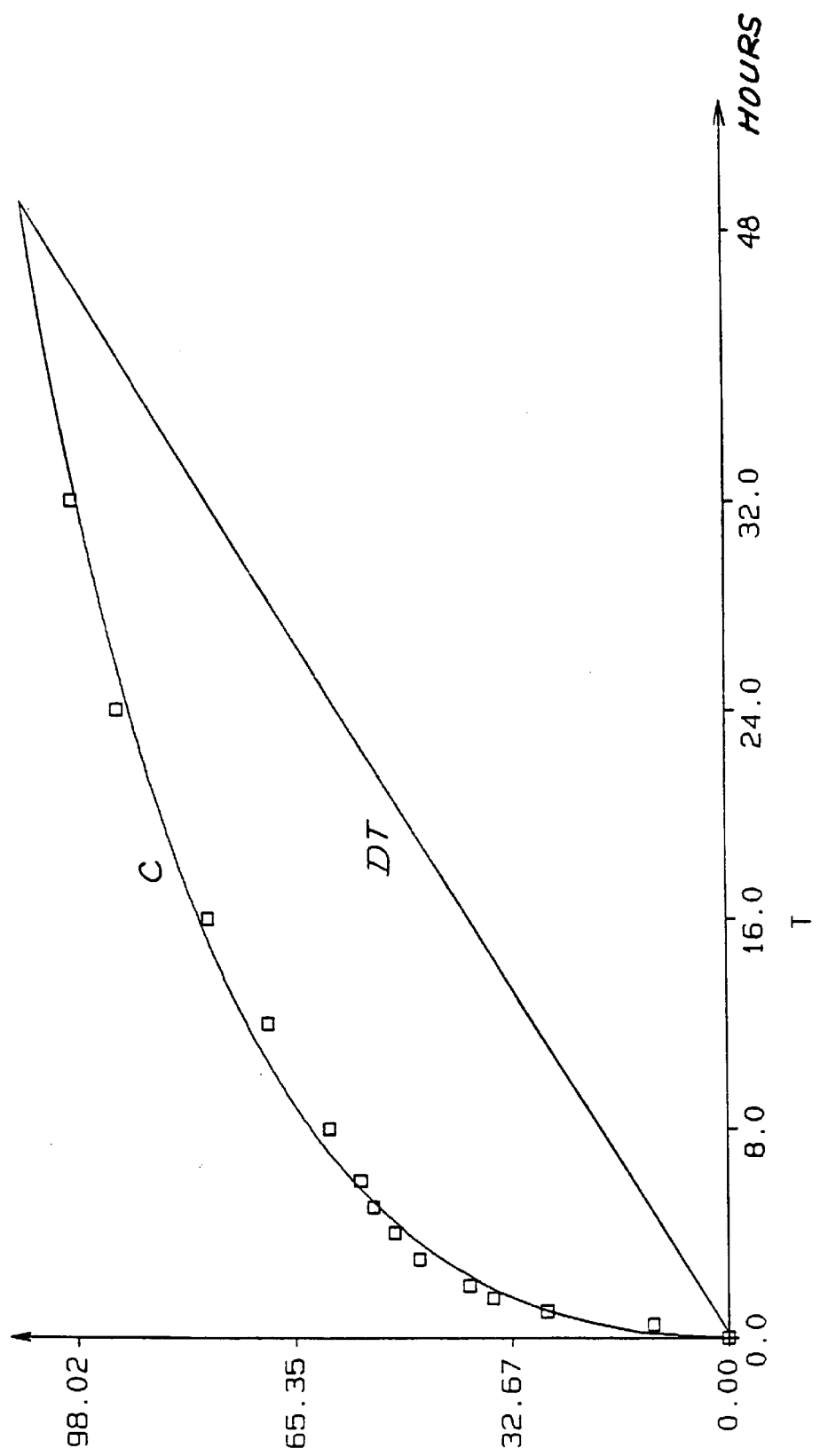
FIG. 1 shows the kinetic profile of the in vivo absorption of ASA.

Thus the Applicant takes the credit for demonstrating, after much testing and research, that the ad hoc pharmaceutical form, as regards the specifications referred to above, advantageously consists of coated particles of ASA of a carefully selected size fraction and with a structure such that the in vivo absorption of the ASA takes place according to a characteristic kinetic profile extending over at least 24 hours for a dose of between 75 and 320 mg, said profile being represented by curve C in FIG. 1 attached.

Consequently, the present invention relates to microcapsules for the controlled release of ASA in the gastrointestinal environment, said microcapsules consisting of particles of acetylsalicylic acid with a size of between 100 and 1000 μm which are coated and designed so that, when ingested per os in a single administration of a dose D of between 75 and 320 mg of ASA, they induce moderate ASA absorption kinetics in vivo in man, extending over at least 24 hours, said ASA absorption being:

less than or equal to 10% of the absorbed fraction of D at a time t after ingestion of 0.4 hour, less than or equal to 50% by weight of the absorbed fraction of D at t=3.9 hours, and less than or equal to 90% by weight of the absorbed fraction of D at t=23 hours, t being given to within±10%.

These advantageous provisions are particularly surprising and unexpected insofar as EP-A-0 377 439 teaches that the known high-dosage forms are unsuitable, and proposes to rectify this by providing a low-dosage system for the controlled release of ASA over 8 hours. It was not therefore an obvious step, a priori, to take a renewed interest in the higher-dosage forms, especially as it was known to what extent the latter were capable of having a deleterious influence on the prostacycline.

In a preferred embodiment of the invention, the absorption takes place over a period of between 24 and 48 hours in the following manner:

10% of the absorbed fraction of D at t=0.4 to 5 hours,

50% of the absorbed fraction of D at t=3.9 to 25 hours, and

90% of the absorbed fraction of D at t=23 to 45 hours.

The curve C of FIG. 1 shows the upper limit of the ASA in vivo absorption profile induced by the microcapsules according to the invention, as a function of time, at a dose of 320 mg.

This absorption is expressed in % absorbed relative to the absorbed fraction of the initial dose D. This curve C is obtained by conventional deconvolution analysis (Milo GIBALDI and D. PERRIER, Pharmacokinetics, 2nd ed., New York, Marcel Dekker Inc., 1983, p. 145–167) from the mean curves of the plasma concentrations as a function of time after the oral administration of 350 mg of ASA equivalents of ASPEGIC® (control form) and 320 mg of ASA equivalents of microcapsules according to the invention in the form of gelatin capsules.

In this case, the tracer molecule chosen for the plasma concentrations as a function of time is necessarily salicylic acid (SA), a metabolite of ASA. The plasma concentrations of SA are determined by HPLC.

The critical points at 0.4, 3.9 and 23 h, given above in the definition of the microcapsules of the invention, are of course to be found on this curve.

Beyond this curve C, the hepatic ASA deacetylation mechanism is saturated. It must be considered that all the ASA in vivo absorption profiles contained in the area under the curve C derive from the invention.

In the preferred embodiment of the invention, the microcapsules have an ASA in vivo absorption profile contained in the area between the curve C and the theoretical straight line DT leading to 100% absorption in 48 hours.

This in vivo absorption curve C, which constitutes one of the essential characteristics of the invention, is a determining factor as regards the intended and achieved result of maximum inhibition of the thromboxane and minimum inhibition of the prostacycline and other prostaglandins.

It is important to note that these remarkable results are obtained without violating the constraints of tolerance, especially gastric tolerance, or the feasibility and industrial viability of the preparation of the microcapsules.

The kinetics of release of the aspirin vary according to the size of the particles of aspirin to be encapsulated.

For example, microcapsules according to the invention obtained from particles of aspirin with a size of 100 $\mu$m, comprising 80% of aspirin and 20% of coating material, release, in vitro, 40 to 50% of the aspirin after 5 hours, 80% after 10 hours, 90% after 16 hours and 100% after 24 hours, in the gastrointestinal environment.

Other microcapsules according to the invention, with a slower release, can be obtained for example from particles of aspirin with a mean size of between 315 and 400 $\mu$m, comprising 80% of aspirin and 20% of coating material, these microcapsules releasing, in vitro, 35% of the aspirin after 5 hours, 60% after 10 hours and 100% after 24 hours, in the gastrointestinal environment.

In a preferred modality of the invention, the particles of ASA used for the coating operation have a size of between 250 and 800 $\mu$m, preferably of between 300 and 500 $\mu$m.

Advantageously, the coating agent represents 5 to 50% by weight, preferably 10 to 40% by weight and particularly preferably 10 to 35% by weight, based on the total mass of the microcapsules.

Naturally, the coating agent forms one of the key aspects of the present invention, given that the in vivo absorption curve described above constitutes a model useful to those skilled in the art for determining with relative ease, e.g. by trial and error, those technical coating characteristics, in particular the nature of the coating agent, which enable the intended pharmacological effect to be achieved.

Advantageously, the coating agent consists of a coating composition comprising:
  at least one film-forming polymer ($P_1$) insoluble in the gastrointestinal environment,
  at least one water-soluble polymer ($P_2$),
  at least one solid lubricating filler, and
  at least one hydrophobic plasticizer.

Another novel feature of the present invention is expressed through the abovementioned coating composition, which consists of a non-arbitrary selection of four compounds whose functionalities combine to give the result intended by the invention.

Preferably, the coating composition is quantitatively defined as follows, expressed in % by dry weight:
  $P_1$: 60 to 85, preferably 70 to 80%,
  $P_2$: 2 to 20, preferably 5 to 15%,
  lubricant: 2 to 20, preferably 8 to 20%,
  plasticizer: 2 to 20, preferably 5 to 15%.

In an advantageous modality of the invention, the film-forming polymer $P_1$ is soluble in at least one organic solvent with a boiling point of between 35 and 120° C.

Advantageously, $P_2$ is a water-soluble polymer which is also soluble in a solvent for $P_1$.

Furthermore, the solid lubricating filler is preferably insoluble in water and in the solvents for $P_1$.

In a variant of the quantitative definition of the coating agent according to the invention, the latter comprises from 10 to 30 parts by weight of the polymer derivative $P_1$, 1 to 3 parts by weight of the polymer derivative $P_2$, 2 to 4 parts by weight of a solid lubricating filler and 1 to 3 parts by weight of a plasticizer.

According to a remarkable characteristic of the invention, $P_1$ is selected from the following products: zein, ethyl cellulose, vinyl chloride, vinyl acetate and/or its copolymers, copolymers based on ethyl and/or methyl acrylate and/or methacrylate, for example the products marketed under the trademark EUDRAGIT® RL and/or RS, and mixtures of all these products.

Without implying a limitation, it should be emphasized that ethyl cellulose is particularly suitable as the compound $P_1$.

$P_2$ is preferably selected from the following products:
  polyvinylpyrrolidone,
  water-soluble cellulose derivatives such as hydroxypropyl cellulose, hydroxypropyl methyl cellulose, hydroxymethyl ethyl cellulose and methyl cellulose,
  vinyl acetate/crotonic acid copolymers,
  maleic anhydride/methyl vinyl ether copolymers, and
  derivatives and mixtures of all the above-mentioned products.

In general, it is polyvinylpyrrolidone which is preferably associated with $P_1$ for carrying out the coating operation according to the invention.

The complementary solid lubricating filler is chosen from the following compounds: alkaline earth metal salts of stearic acid, magnesium silicates, kaolin, talc, silica and mixtures thereof.

The final constituent of the composition according to the invention is the plasticizer, which consists of at least one of the following products:
  stearates of a glycol such as glycerol, propylene glycol or triacetin,
  citrates,
  phthalates, for example dimethyl, diethyl or
  dibutyl phthalate,
  esters of cetyl alcohol, such as cetyl palmitate in particular,
  sebacates,
  tartrates,
  castor oil,
  cutin, and
  synthetic resins, for example Cérit.

The preferred solid lubricating filler and preferred plasticizer are magnesium stearate and castor oil respectively.

As an example of a coating composition which is more readily used, there may be mentioned the composition comprising ethyl cellulose ($P_1$)/polyvinylpyrrolidone ($P_2$)/magnesium stearate/castor oil, the respective components being present in the following preferred relative proportions by dry weight:
  74±2,
  8±2,
  10±2,
  8±2%.

This coating composition constitutes one of the novel features of the present invention. It is characterized by an intimate combination of the four compounds indicated above.

To prevent the problems of caking of the coated particles constituting the microcapsules of the invention, provision is advantageously made for adding thereto at least one anticaking agent preferably formed of talc, colloidal silica or a mixture of the two.

In general, the particles of ASA according to the invention are coated by being sprayed with the intimate combination forming the coating agent, suspended in an organic solvent or mixture of organic solvents.

The coating process, which constitutes a further subject of the invention, fits into the general pattern of microencapsulation techniques, of which the main ones are summarized in the article by C. DUVERNEY and J.P. BENOIT in "L'actualitéchimique", December 1986. More precisely, the technique in question is microencapsulation by film coating.

Preferably, this process consists essentially in:

a) preparing the coating composition by mixing $P_1$, $P_2$. the lubricant and the plasticizer in a solvent system, b) applying the composition/solvent system mixture to particles of acetylsalicylic acid, c) drying the resulting microcapsules, and d) if appropriate, mixing the latter with at least one anticaking agent.

Examples of solvents which are suitable for forming part of the composition of the solvent system are ketones, esters, chlorinated solvents, alcohols, preferably aliphatic alcohols, alkanes or mixtures thereof.

These solvents are advantageously $C_1$–$C_6$ compounds and particularly preferably acetone, methyl ethyl ketone, methanol, ethanol, isopropanol, cyclohexane and methylene chloride.

If the coating methodology which can be used according to the invention is considered in greater detail, it can be stated that the coating composition/solvent system mixture is applied by being sprayed onto the moving particles of ASA, said movement preferably being created by mechanical agitation or by blowing (fluidization).

To obtain microcapsules according to the invention possessing the desired absorption kinetics, it is necessary to encapsulate particles of ASA with a mean size of between 75 and 500 μm, preferably of between 300 and 500 μm, for a dose D of between 75 and 320 mg.

In a preferred mode of carrying out the process according to the invention for the microencapsulation of particles of aspirin, provision is made for the following steps:

$a_1$) first of all, a mixture is prepared which comprises from 10 to 30 parts by weight of a film-forming polymer $P_1$ and 1 to 3 parts by weight of a plasticizer per 1 to 3 parts by weight of a water-soluble polymer $P_2$ in solution, either in an acetone/alkanol mixture such that the acetone/alkanol ratio is between 50/50 and 70/30 (v/v), or in a solvent selected from cyclohexane, toluene, carbon tetrachloride, chloroform and methylene chloride;

$a_2$) 2 to 4 parts by weight of lubricant, based on 1 to 3 parts by weight of vinylic polymer $P_2$, are suspended in the solution prepared in the previous step;

b) the resulting mixture is sprayed onto the microparticles of active principle in a fluidized bed;

c) the microcapsules are dried at the end of the spraying step in the fluidized bed and then in an oven; and d) the resulting microcapsules are mixed with 0.5 to 2 parts by weight of antiadherent, based on 1 to 3 parts by weight of vinylic polymer $P_2$.

Preferably, in step b), either the same alkanol is added to give an acetone/alkanol ratio of 60/40 (v/v), or the same solvent is added.

In the present description, alkanol is understood as meaning an aliphatic alcohol having from 1 to 6 carbon atoms, isopropanol being preferred.

In a preferred mode of carrying out the process according to the invention, the microcapsules are dried after coating.

The microcapsules described above, which may have been obtained by the process also explained above, can be used for the preparation of novel galenical forms of aspirin having a biochemical selectivity for the inhibition of thromboxane relative to the other prostaglandins, in particular for the preparation of novel galenical forms useful as platelet aggregation inhibitors, and/or, more precisely, for the preparation of novel galenical forms active in the prevention and/or treatment of cardiovascular diseases and risks.

The present invention further relates to these novel galenical forms as such, being novel in their structure, their presentation and their composition. Advantageously, they are presented in the form of tablets, powders or gelatin capsules containing 20 to 500 mg, preferably 50 to 400 mg and particularly preferably 75 to 320 mg of active principle. Such galenical forms are preferably administered per os in single daily doses each comprising between 75 and 320 mg of ASA equivalents.

It should be noted that it can be of value to mix, in one and the same gelatin capsule, tablet or powder, at least two types of microcapsules whose absorption kinetics are different but within the framework characteristic of the invention (profile of curve C of FIG. 1).

According to another of its features, the invention relates to a method of preventing and/or treating pathological disorders associated with excesses of thromboxane, particularly cardiovascular diseases and risks. This method consists in the oral administration of the microcapsules and/or galenical forms according to the invention, preferably in a single daily dose of between 75 and 320 mg of ASA equivalents.

It is apparent from the foregoing text that the microcapsules of the invention are very effective in pharmacological terms, perfectly tolerated by the organism, especially as regards gastric tolerance, capable. of being presented in various appropriate galenical forms and, finally, easy and inexpensive to obtain.

The invention will be understood more clearly from the following Examples, which are given solely by way of illustration and serve to provide a clear understanding of the invention and to illustrate its different embodiments and/or modes of implementation, as well as its various advantages.

EXAMPLES

Example 1
Preparation of Aspirin-based Microcapsules by Encapsulation in a Fluidized-bed Granulator
1.1 Microcapsules $M_1$:

To coat 160 mg of microparticles of aspirin, 21.5 mg of ethyl cellulose (standards USP XXII), 2 mg of polyvidone (French Pharmacopoeia, 10th edition) and 2 mg of castor oil (French Pharmacopoeia, 10th edition) are dissolved in 311 mg of acetone. 208 mg of isopropanol are added to the solution obtained. 3 mg of magnesium stearate are then suspended in the solution. The resulting mixture is agitated and this agitation is maintained throughout the subsequent coating operation.

2110 g of microparticles of aspirin (mean size 150 μm) are charged into a GLATT GPCG 3 fluidized-bed apparatus and fluidized at a flow rate of 1.16 to 2 m³/min. The temperature of the air entering the fluidized bed is 55° C. and is kept constant.

7219 g of the coating suspension described above, maintained under constant agitation, are sent via a peristaltic pump to an injection nozzle of diameter 1.2 mm and sprayed continuously onto the microparticles at a spraying pressure of $2.8 \times 10^5$ Pa.

After a preheating phase of about 10 min., the output of the peristaltic pump is adjusted so as to spray 30 g of coating suspension per minute.

The microcapsules are then dried for 15 to 30 min. at a reduced fluidization flow rate (1.16 m$^3$/min.). They are then removed from the chamber and spread out on trays, which are placed in an oven at a temperature of 50° C. for about 1 hour.

1.2 Microcapsules $M_2$:

2100 g of microparticles of ASA with a size of between 300 and 500 µ are film-coated in the GLATT GPCG 3 apparatus, as described above for $M_1$, with a coating suspension of the following composition:

| | |
|---|---|
| EUDRAGIT RS 100 | 362.8 g |
| Dibutyl phthalate | 36.2 g |
| Micronized talc | 107.1 g |
| Hydroxypropyl methyl cellulose | 18.4 g |
| Acetone | 2902.0 g |
| Isopropanol | 4353.0 g |

1.3 Microcapsules $M_3$:

2110 g of microparticles of ASA with a size of between 300 and 500 µ are film-coated in the GLATT GPCG 3 apparatus, as described above for $M_1$, with a coating suspension of the following composition:

| | |
|---|---|
| Zein | 308.7 g |
| Glycerol triacetate | 30.9 g |
| Micronized talc | 92.6 g |
| Magnesium stearate | 58.9 g |
| Polyvinylpyrrolidone | 30.9 g |
| Methylene chloride | 3087.0 g |
| Methanol | 3087.0 g |

Example 2

Preparation of a Pharmaceutical Form Based on the Microcapsules of ASA according to the Invention The microcapsules $M_1$ obtained by the process described in Example 1 are then mixed with colloidal silica and talc.

The resulting mixture is then distributed into size 0, 1 or 2 gelatin capsules according to the desired unit dosage (320, 160 or 80 mg).

The encapsulating machine used is a Zanussi L 264 with a maximum capacity of 5000 units per hour. The gelatin capsules have been checked beforehand (color, quantity) and the units are checked during the encapsulation process. The final product is then checked according to the new specifications defined and adapted for each product: appearance, average weight, dosage, disintegration, dissolution, assay of the impurities.

Example 3

Analytical Determination of the Rate of Dissolution of the Microcapsules

The dissolution of the microcapsules, gelatin capsules or tablets in vitro was checked according to the instructions in the European Pharmacopoeia, 2nd edition, entitled: "Essai de la dissolution des formes orales solides" ("Testing the dissolution of solid oral forms"). The basket apparatus was used for the finished forms (gelatin capsules and tablets). The basket apparatus was chosen for measuring the dissolution of the microcapsules. The basket apparatus consists of a cylindrical vessel, a stirrer and a thermostatically controlled bath. The dissolution medium is a phosphate buffer of pH 7.2, prepared according to the recommendation in the Pharmacopoeia. A control solution of aspirin is prepared by dissolving 61 mg of active principle in the medium of pH 7.2, made up to 20 ml. The study is performed in 900 ml of the dissolution medium at 37° C.±0.5 and at a speed of rotation of 100 rpm. The equivalent of one gelatin capsule is introduced into the dissolution medium and 10 ml of the medium are taken 0, 1, 2, 4, 6, 8, 12 and 24 hours after the start of the experiment. In view of the possible hydrolysis of ASA to SA, the amount of aspirin dissolved is determined by measurement of the absorbance at the isobestic point of ASA and SA at 265 nm.

Figure 2:
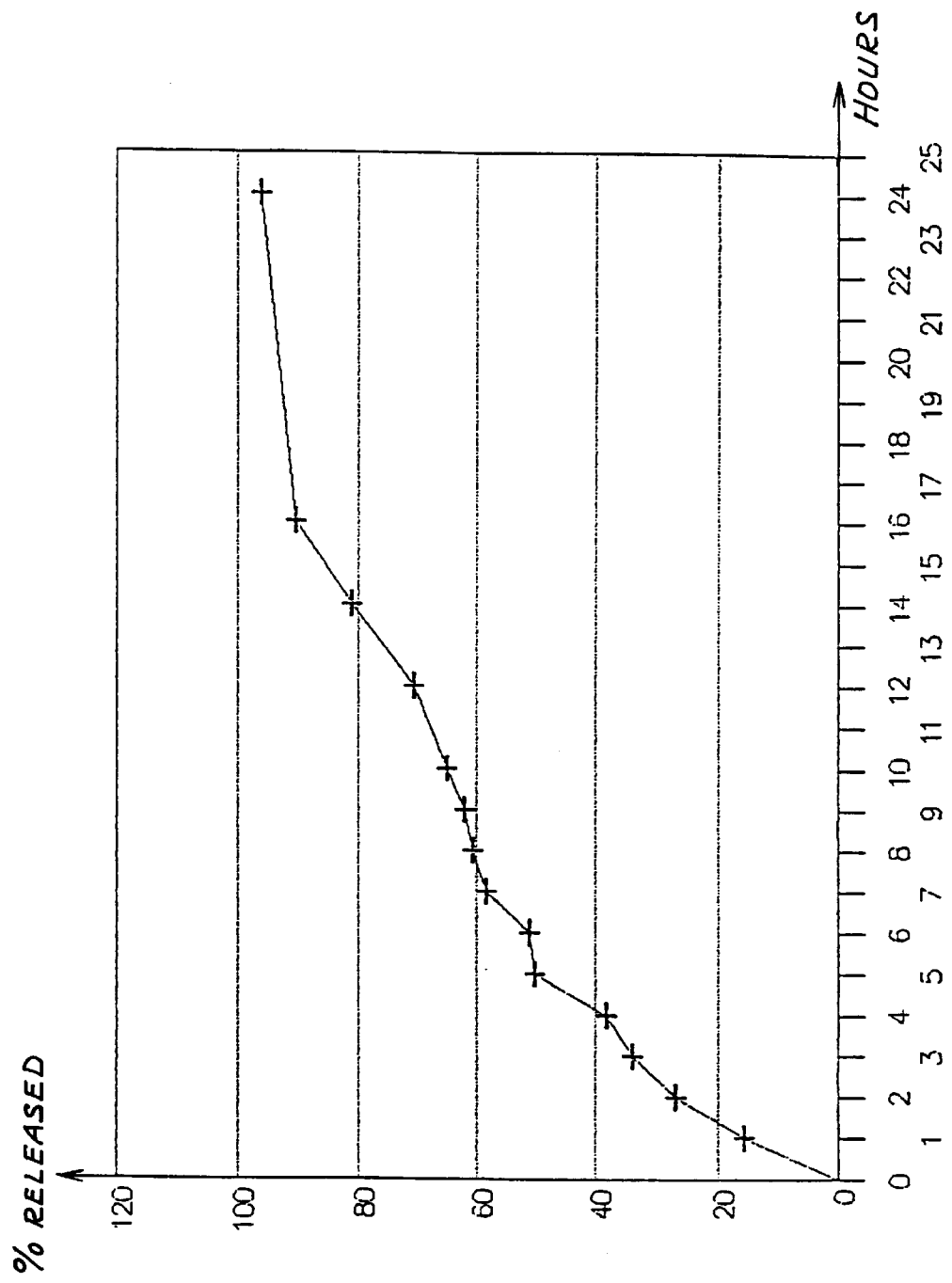
FIG. 2 shows the percentage of aspirin released as a function of time for the microcapsules $M_1$.

FIG. 2 shows the percentage of aspirin released as a function of time for the microcapsules $M_1$ of Example 1, determined on a batch of 40 kg.

Figure 3:
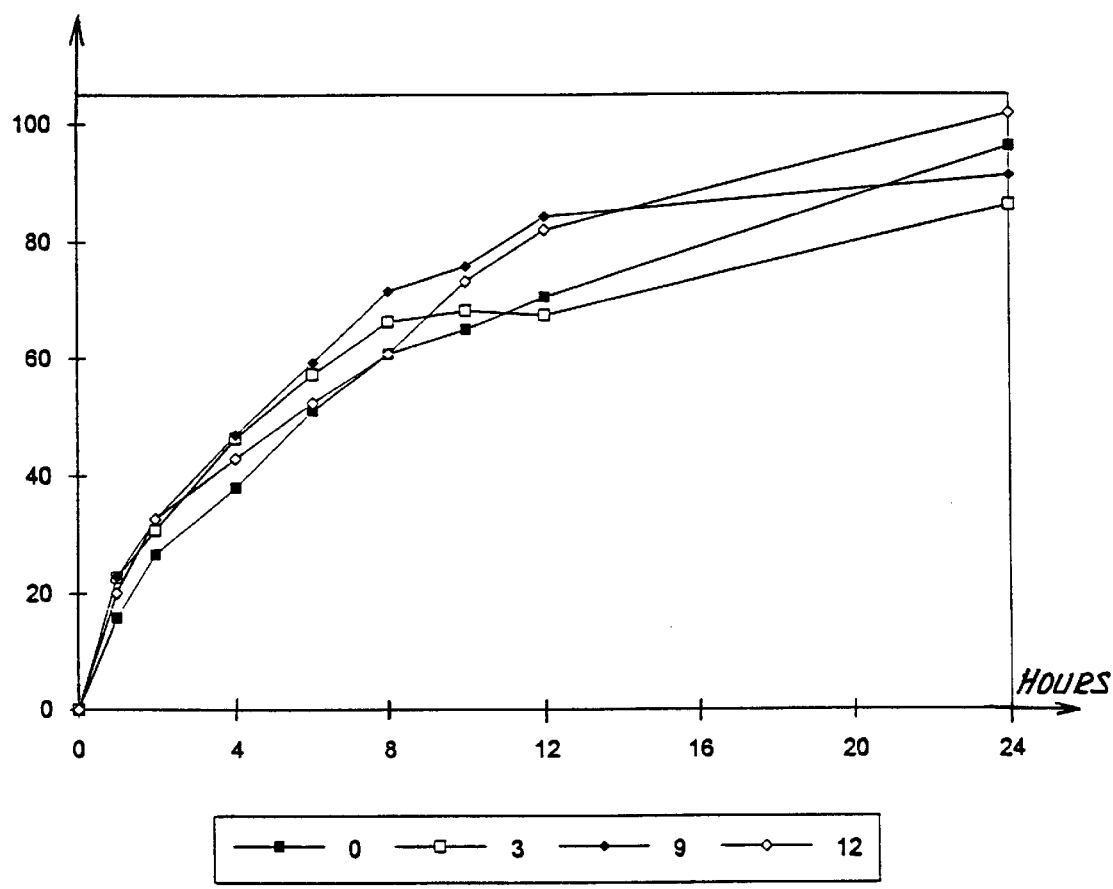
FIG. 3 shows the release profile, after 0, 3, 9 and 12 months of stability.

FIG. 3 shows the release profile, under the conditions described above, determined after 0, 3, 9 and 12 months of stability.

Example 4

Toxicological Study of Controlled-release Encapsulated Aspirin (CRA)

The microcapsules of aspirin $M_1$ prepared according to Example 1 were subjected to a toxicological study by comparison with commercial aspirin (CA) in the form of a white powder. The acute toxicity of these two pharmaceutical forms of aspirin was evaluated and compared by oral administration to rats.

a) Methods:

Each of the two formulations of the product was administered orally to groups of 10 Sprague-Dawley rats (5 males and 5 females) in a volume of 10 ml/kg and in suspension in 0.5% carboxymethyl cellulose. The controlled-release aspirin according to the invention was administered at a dose of 2500 mg/kg and the commercial aspirin at doses of 740, 1110, 1670 and 2500 mg/kg. All the animals were placed on a water diet before the treatment.

The mortality, the general behavior and the weight change of the surviving animals were followed for a period of 14 days after the single administration of the product. An anatomicopathological examination was carried out on each of the animals found dead or sacrificed at the end of the study.

The $LD_{50}$ was calculated by Finney's method.

b) Results:

* CA:

After administration of the CA product at doses of 740, 1110, 1670 and 2500 mg/kg, a drop in the spontaneous activity, related to the dose administered, and piloerection were observed over the hours following the treatment.

A slight drop in the weight gain, related to the dose administered, was noted between day 1 and day 5, with no consequences thereafter up to the end of the study.

In the autopsy of the animals found dead during the study, no macroscopic anomalies were noted at the 740 and 1110 mg/kg doses. The animals found dead in the hours following the administration of the 1670 and 2500 mg/kg doses were observed to have an abnormally blackish coloration of the liver, a discoloration with wall thickening in the digestive tract (intestines and stomach) and reddish petechiae in the stomach. These signs are characteristic of pronounced gastric intolerance.

* CRA:

The general behavior and the weight change of the animals treated with CRA at a dose of 2500 mg/kg are normal throughout the study.

The autopsy of the animals found dead or sacrificed at the end of the study did not reveal any macroscopically visible anomalies.

c) Conclusion:

Under the experimental conditions, the $LD_{50}$ of the CA product, administered orally to rats, is 1432 mg/kg. The lower and upper limits of the confidence interval for a probability threshold of 95% were 936 mg/kg and 2394 mg/kg respectively. The $LD_{50}$ of the CRA product according to the invention, administered orally to rats, was greater than or equal to 2500 mg/kg, at which dose no behavioral anomalies or anomalies in the principal organs were observed.

Example 5
Pharmacokinetic Study of Controlled-release Encapsulated Aspirin over 32 Hours Trials were carried out on humans to determine the bioavailability of the microcapsules according to the invention and to verify the degree of inhibition of the platelet cyclooxygenase by measurement of the serum thromboxane $B_2$.

For greater convenience, the following abbreviations will be used hereafter:

CRA: controlled-release encapsulated aspirin according to the invention ($M_1$ of Example 1), ASA: acetylsalicylic acid, SA: salicylic acid.

The pharmacokinetic study was performed on twelve male volunteers who were not suffering from any hemobiochemical, hemorrhagic, allergic or gastrointestinal complaints, did not smoke more than 10 cigarettes a day and had not participated in a therapeutic trial or donated blood in the three months preceding the study. These subjects had not received any drugs in the 15 days preceding the study.

Each subject received 2 gelatin capsules of CRA with 250 ml of water, each gelatin capsule corresponding to 160 mg of ASA, or 2 sachets of ASPEGIC (1 sachet containing a 250 mg dose and one sachet containing a 100 mg dose, i.e. 350 mg of ASA).

The gelatin capsules or sachets were taken after at least 10 hours of fasting.

A meal was served 4 hours after administration of the drug.

a) Determination of the Active Principle in the Plasma:

Blood samples were taken from the subjects prior to administration of the drug and 0.5, 1, 1.5, 2, 3, 4, 5, 6, 8, 12, 16, 24 and 32 hours after the treatment.

The ASA and SA in the plasma were assayed by a method adapted from that of R. JAMES et al. (R. JAMES et al., J. Chrom. Biomed. Appl., 1984, 310, 343–352) and summarized below.

50 µl of an internal standard solution (3,4,5-trimethoxybenzaldehyde, 25 µg/ml) and 50 µl of 30% perchloric acid are added to 0.5 ml of plasma, which contains potassium fluoride to prevent hydrolysis of the aspirin.

The mixture is agitated for 30 seconds on a Vortex and centrifuged for 5 min. at 3000 rpm. About 20 µl of the supernatant phase are used for chromatographic analysis.

Separation is effected on a Lichrospher 100 RP-18 column, 5 µm, 250×4 mm (Merck), with a mobile phase of acetonitrile/methanol/0.085% $H_3PO_4$ (10/40/50 v/v/v). The flow rate of the mobile phase is fixed at 1 ml/min. and detection is performed in the UV at 230 nm.

The mean plasma concentrations of ASA and SA were determined and are collated in Table 1 below:

TABLE 1

MEAN PLASMA CONCENTRATIONS OF ASA AND SA

| TIME (h) | MPC of ASA (µg/ml) | | MPC of SA (µg/ml) | |
|---|---|---|---|---|
| | CRA | ASPEGIC | CRA | ASPEGIC |
| 0 | 0 | 0 | 0 | 0 |
| 0.5 | 0.59 | 5.88 | 1.11 | 18.9 |
| 1 | 0.62 | 1.31 | 2.60 | 18.6 |
| 1.5 | 0.44 | 0.43 | 3.27 | 17.0 |
| 2 | 0.29 | 0.18 | 3.41 | 14.3 |
| 3 | 0.07* | nq | 3.49 | 11.7 |
| 4 | nq | nq | 3.20 | 9.05 |
| 5 | nq | nd | 2.85 | 7.10 |
| 6 | nd | nd | 2.43 | 5.28 |
| 8 | nd | nd | 1.84 | 2.87 |
| 12 | nd | nd | 1.34 | 0.94 |
| 16 | nd | nd | 1.13 | 0.25 |
| 24 | nd | nd | 0.83 | nq |
| 32 | nd | nd | 0.43 | nq |

MPC: mean plasma concentration,
nq: not quantifiable,
nd: not detected,
*: below the sensitivity limit.

These results are illustrated in FIGS. 4 and 5 attached, which show the change in the mean plasma concentrations in micrograms/ml of ASA and SA, respectively, as a function of time (CRA and ASPEGIC control).

Acetylsalicylic acid is detectable in the plasma up to 2 hours and then after 4 and 5 hours at very low concentrations less than or equal to 0.25 µg/ml. Salicylic acid is detectable very rapidly at concentrations which rise until they reach a pseudo plateau (from 0.8 to 1.8 µg/ml) between 8 and 24 hours.

The AUC (areas under the curve) show that the bioavailability of CRA relative to ASPEGIC is about 72%. Furthermore, SA is detectable only up to 16 hours after the administration of ASPEGIC, whereas it is still detectable 32 hours after the administration of CRA.

These results show that the microcapsules according to the invention make it possible to obtain controlled-release kinetics which are such that the acetylsalicylic acid is entirely deacetylated during the first passage through the liver, resulting in inhibition of the platelet cyclooxygenase while leaving the activity of the peripheral cyclooxygenase intact.

b) Assay of the Thromboxane $B_2$ in the Serum (CRA Only):

Blood samples were taken from the subjects 1, 2, 3, 4, 5, 6, 8, 12, 16, 24 and 32 hours after the treatment. The samples are placed in a water bath (37° C.) for 1 hour and then centrifuged. The serum is then removed and divided up into 2 tubes, which are frozen until required for analysis.

The method of measuring the thromboxane $B_2$ is an enzyme immunoassay using specific anti-thromboxane antibodies and a corresponding enzyme tracer, namely thromboxane $B_2$ coupled with acetylcholinesterase.

This is a competitive assay using microtiter plates containing 96 wells covered with anti-rabbit IgG monoclonal mouse immunoglobulins. The specific anti-thromboxane $B_2$ antibody, the standard or the biological sample and the tracer are added in volumes of 50 µl.

The reactions and dilutions are carried out in a phosphate buffer containing albumin. After incubation overnight at 4° C., the plates are washed and the enzymic substrate containing Ellman's reagent is then distributed into each well. After shaking to develop the coloration, the absorbance is measured after 2. hours at 414 nm with the aid of a spectrophotometer.

The coloration developed is proportional to the amount of thromboxane $B_2$ present in the sample. The results obtained are collated in Table 2 below:

TABLE 2

SERUM CONCENTRATION OF THROMBOXANE $B_2$

| TIME (h) | CONCENTRATION (ng/ml) | % INHIBITION |
| --- | --- | --- |
| 0 | 300.53 | — |
| 1 | 91.65 | 69.5 |
| 2 | 56.76 | 81.1 |
| 3 | 34.29 | 88.6 |
| 4 | 26.60 | 91.1 |
| 5 | 31.72 | 89.4 |
| 6 | 25.44 | 91.5 |
| 8 | 12.43 | 95.9 |
| 12 | 12.61 | 95.4 |
| 16 | 19.51 | 93.5 |
| 24 | 28.90 | 90.4 |
| 32 | 35.35 | 88.2 |

The maximum inhibition after the administration of 320 mg of encapsulated aspirin according to the invention is obtained after 8 hours and is still high (88.2%) 32 hours after administration.

The concentration of thromboxane $B_2$ in the serum drops rapidly, proving that the formulation according to the invention effectively releases ASA, which, by contrast, is not found in the general circulation.

This confirms that the administration of the controlled-release aspirin-based microcapsules according to the invention makes it possible to inhibit the platelet cyclooxygenase.

Example 6
Study of the Pharmacokinetics and Clinical Pharmacology of the Coated Microencapsulated ASA According to the Invention After Repeated Administration for 28 Days, and Comparison with a Conventional Form.

Twelve healthy male volunteers were assigned to one or other of the following two treatments according to a randomization schedule obtained by drawing lots. Group A received one 320 mg gelatin capsule of encapsulated ASA (microcapsules $M_1$ of Example 1) orally every morning for 28 days. Group B received 350 mg of non-encapsulated control ASA in solution every morning for 28 days.

In both cases, the subjects took the treatments with 200 ml of water.

The subjects were divided into three groups, which started the study on different dates. During each period, blood samples (5 ml) were taken from each subject for assay of the aspirin and its metabolite, salicylic acid, before administration of the treatment on D1 and D28, on D1 at the following times (H0 being the precise time of administration of the treatment): 5 min., 10 min., 15 min., H0.5, H1, H2, H3, H4, H5, H6, H8, H12 and H16, on D5 and D14 at H0.5, H1, H2, H3, H4, H5, H6, H8, H12 an d H16, on D28 at identical times to those of D5 and D14 followed by H24, H36 and H48, and on D42 one sample was taken early in the morning.

Samples (5 cl) for measurement of the serum thromboxane $B_2$ were taken before administration of the daily treatment on D1, D2, D3, D4, D5, D14, D21, D27, D28 and D42.

The blood samples for the assays of the aspirin and its metabolite, salicylic acid, were taken with a syringe through a short intravenous catheter on D1, D5, D14 and D28 and by direct puncture every other day before administration of the daily treatment. The blood was immediately poured into Vacutainer tubes placed in ice, containing 50 $\mu$l of sodium heparinate (1000 units/ml) and 50 $\mu$l of a 50% aqueous solution of sodium fluoride, which were shaken gently for 2 min. and then centrifuged at 6000 rpm for 3 min. at 4° C. The plasma, separated rapidly from the globular residue, was transferred to two appropriately labeled glass tubes, which were then frozen immediately at −20° C.

a) Urine Samples:

During each period, urine samples were taken from each subject for assaying the creatininuria and measuring the platelet and vascular prostaglandins.

The morning urine was collected at 7 am on days D1, D2, D14, D27 and D28. The subjects were asked to empty their bladder between midnight and 1 am and then not to urinate again until the morning so that the 6-hour urine could be obtained. The morning urination was performed before the subjects got up. Of each sample collected:

20 ml were analyzed for performing a creatininuria assay,
40 ml were transferred to two appropriately labeled 20 ml polypropylene tubes, which were then frozen immediately at −20° C.

b) Measurement of the Bleeding Time:

The bleeding time was measured on D0 and then on D27 during each period, immediately before administration of the treatment.

Method: The bleeding time was measured by Duke's technique: incision of the skin on the front of the ear lobe, disinfected with ether beforehand. A chronometer was then started. The drops of blood formed were collected every 30 seconds on a piece of blotting paper without pressing. The bleeding time is the time after which bleeding stops.

c) Gastric Tolerance:

On D28 during each period, the gastric tolerance was evaluated by gastroscopy.

If one or more substantial lesions were observed, the subject had to be excluded from the study.

The aspirin and salicylic acid were analyzed using an HPLC method specially developed for assaying low levels in biological media. The serum thromboxane $B_2$ was analyzed using an enzyme immunoassay method described by PRADELLES et al. [Analytical Chemistry 57, 1170–1173 (1985); Ann. Biol. Clin. 43, 475–484 (1985)]. For the urine samples, the 11-dehydrothromboxane $B_2$, dinorthromboxane $B_2$ and dinor-6-ketoprostaglandin F1$\alpha$ were analyzed by the method cited above, with prior extraction in the solid phase and purification by thin layer chromatography. This method was validated by gas chromatography coupled with mass spectrometry using a negative ion ionization detector [LELLOUCHE et al., Prostaglandine 40, 297-310 (1990)].

Figure 6:
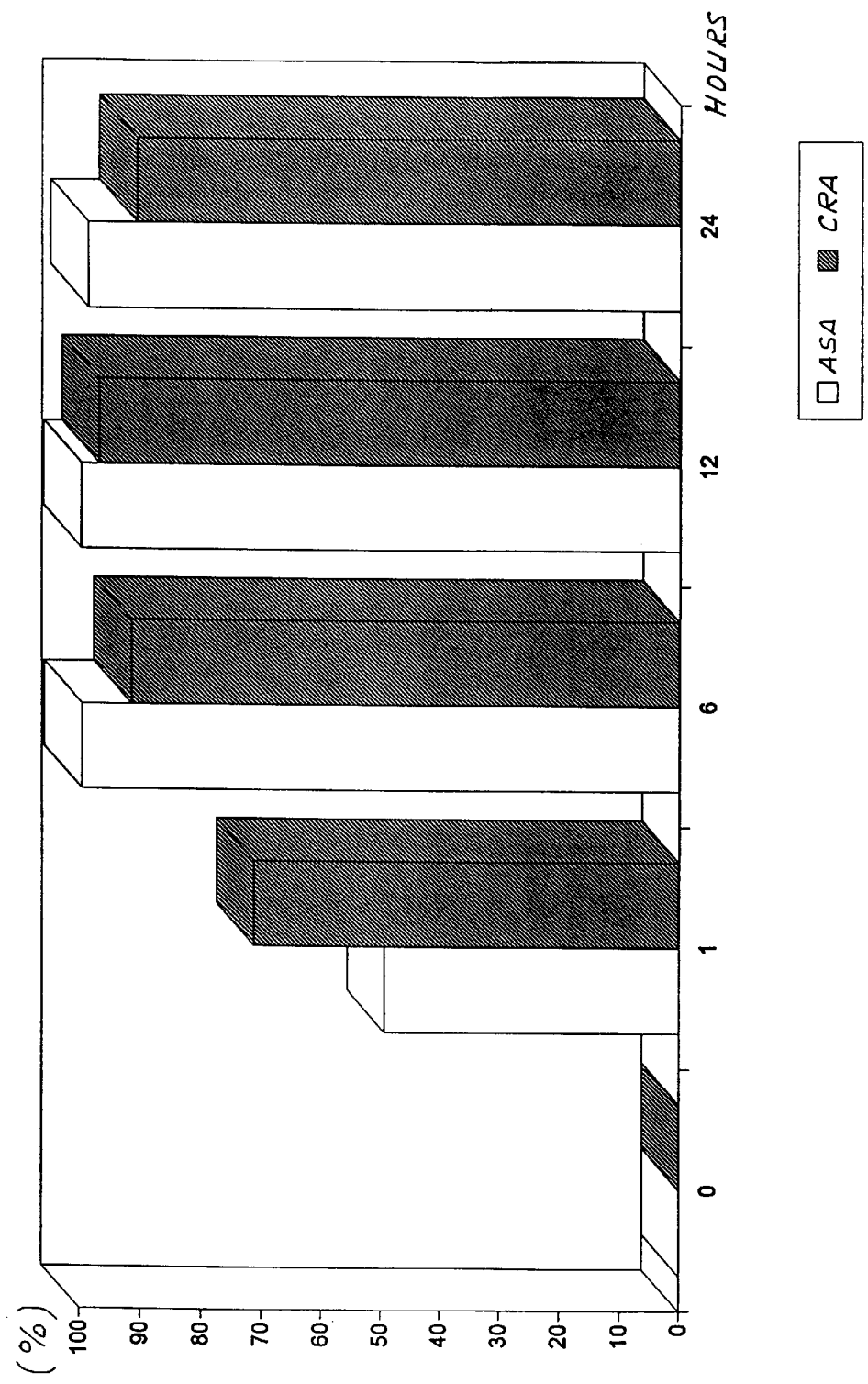
FIG. 6 shows the percentage of inhibition of the production of serum thromboxane $B_2$ by the encapsulated ASA.

FIG. 6 shows the percentage inhibition of the production of serum thromboxane $B_2$ by the encapsulated ASA (CRA) and by the control ASA.

FIGS. 7 and 8 show the inhibition of thromboxane $B_2$, on days D0, D1, D2, D3, D4, D5, D14, D27, D28 and D42, by the control ASA and the CRA respectively. The standard deviation of the concentration is shown on each bar of the histogram. The symbol * indicates the significant nature, from the statistical point of view, of the drop in the thromboxane level relative to the control day D0. These conventional notations are also used on some of the other Figures below.

Thromboxane $B_2$ is a metabolite of thromboxane $A_2$, whose synthesis is catalyzed by the platelet cyclooxygenase.

Figure 9:
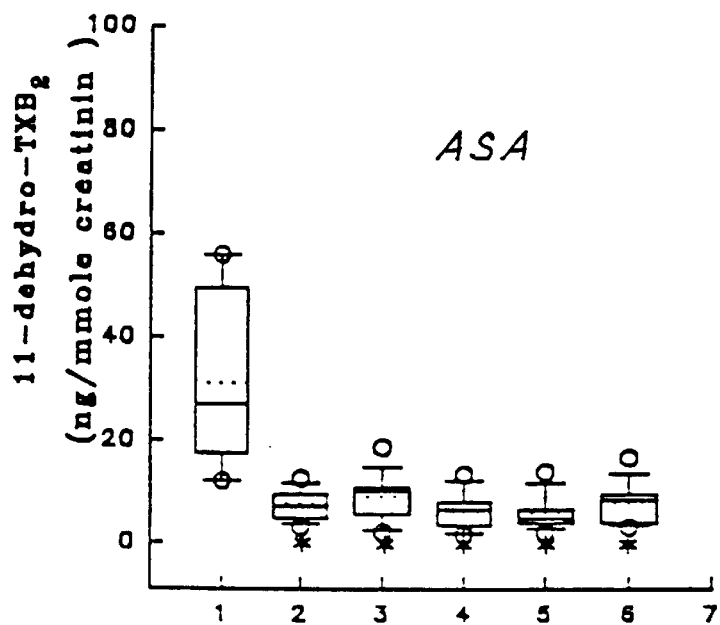
FIGS. 9 and 10 show the inhibition of the production of 11-dehydrothromboxane $B_2$, by the control ASA and the CRA.
Figure 10:
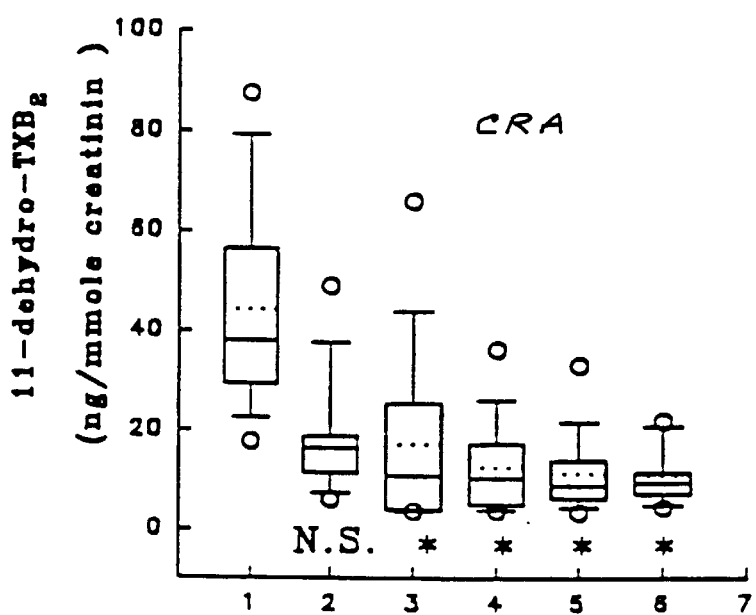

FIGS. 9 and 10 show the inhibition of the production of 11-dehydrothromboxane $B_2$, by the control ASA and the CRA respectively, at different measurement times—D0, D1, D14, D21, D27 and D28 —corresponding to the numbers 1 to 7 on the abscissa.

Figure 11:
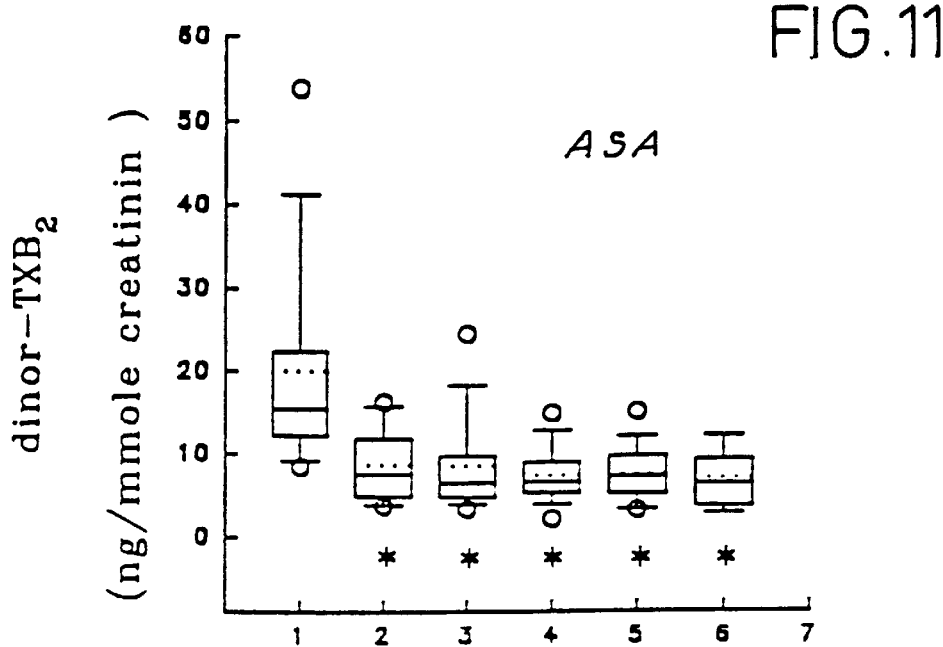
FIGS. 11 and 12 show the inhibition of the production of urinary dinorthromboxane $B_2$.
Figure 12:
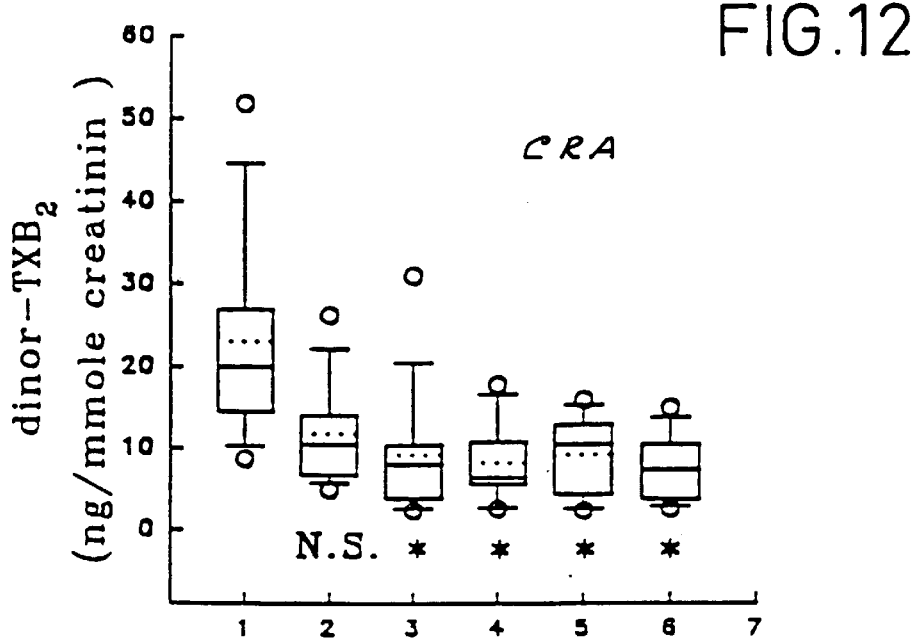

FIGS. 11 and 12 show the inhibition of the production of urinary dinorthromboxane $B_2$, by the control ASA and the encapsulated ASA (CRA) respectively, at different measurement times—D0, D1, D14, D21, D27 and D28—corresponding to the numbers 1 to 7 on the abscissa.

These are two urinary metabolites of thromboxane $B_2$, although 20% of the urinary excretion of 2,3-dinorthromboxane does not originate from the platelets.

FIGS. 13 and 14 demonstrate the effect of the control ASA and the encapsulated ASA (CRA), respectively, on the inhibition of urinary dinor-6-ketoprostaglandin $F1\alpha$ for each of the urine collection times on D0, D1, D14, D21, D27 and D28, corresponding to the numbers U0 to U5 on the abscissa.

2,3-Dinor-6-ketoprostaglandin $F1\alpha$ is the urinary metabolite of prostacycline (prostaglandin I2) of vascular and gastric origin.

Figure 15:
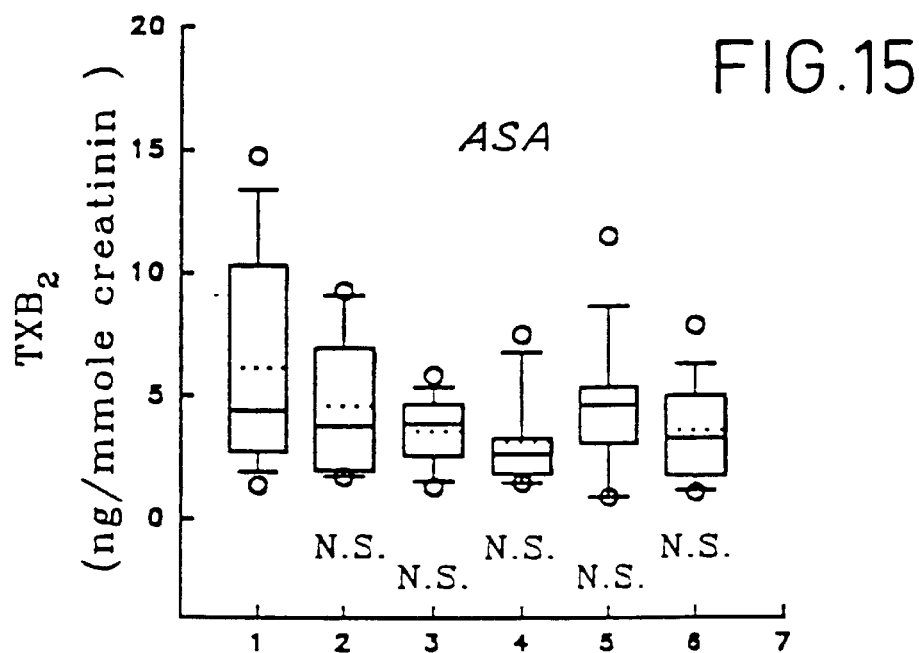
FIGS. 15 and 16 show the influence of the treatments with control ASA and encapsulated ASA on the urinary excretion of thromboxane $B_2$.
Figure 16:
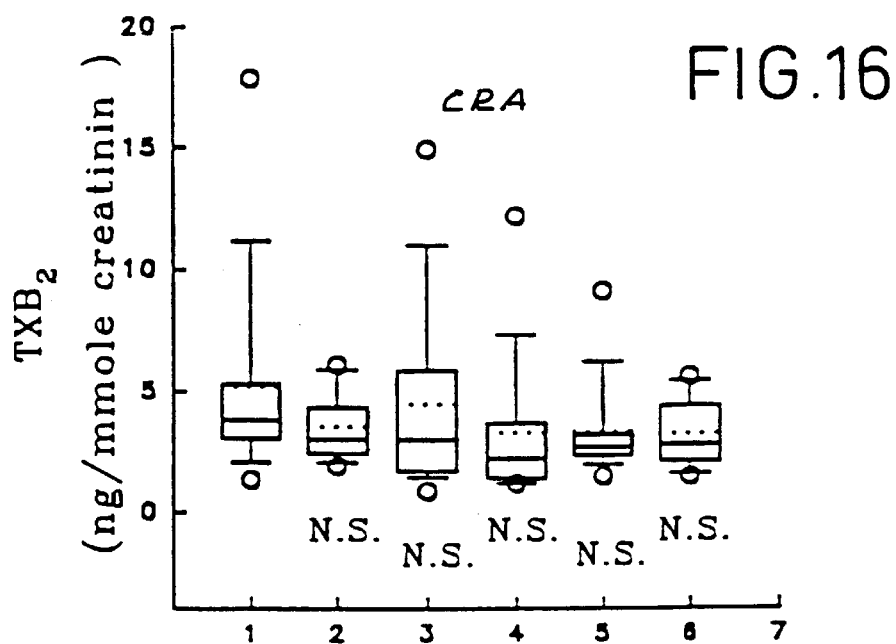

FIGS. 15 and 16 show the influence of the treatments with control ASA and encapsulated ASA (CRA), respectively, on the urinary excretion of thromboxane $B_2$ at the times D0, D1, D14, D21, D27 and D28, corresponding to the numbers 1 to 7 on the abscissa.

Figure 17:
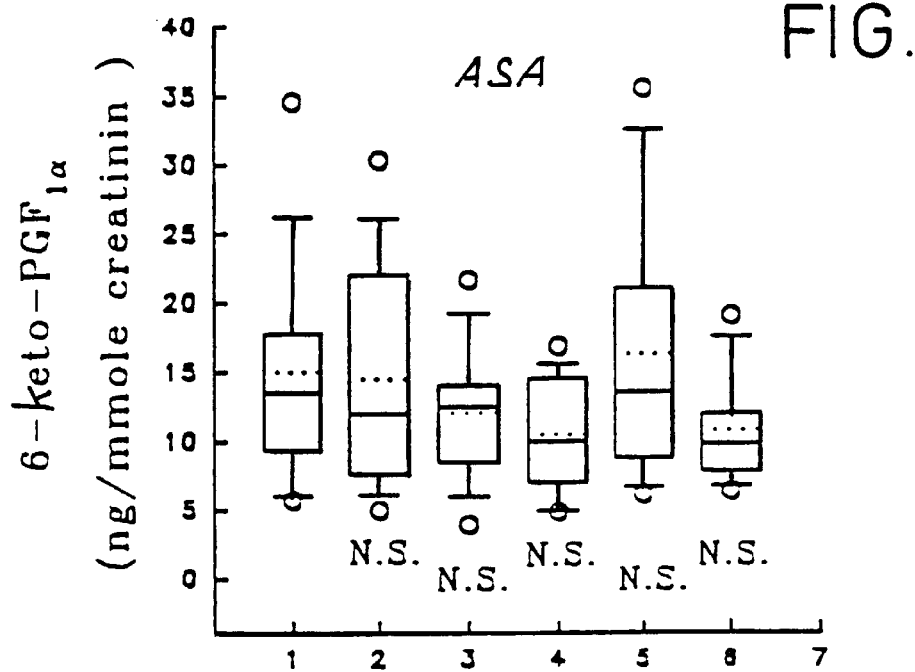
FIGS. 17 and 18 show the influence of the treatments with control ASA and CRA, on the urinary excretion of 6-ketoprostaglandin F1 α.
Figure 18:
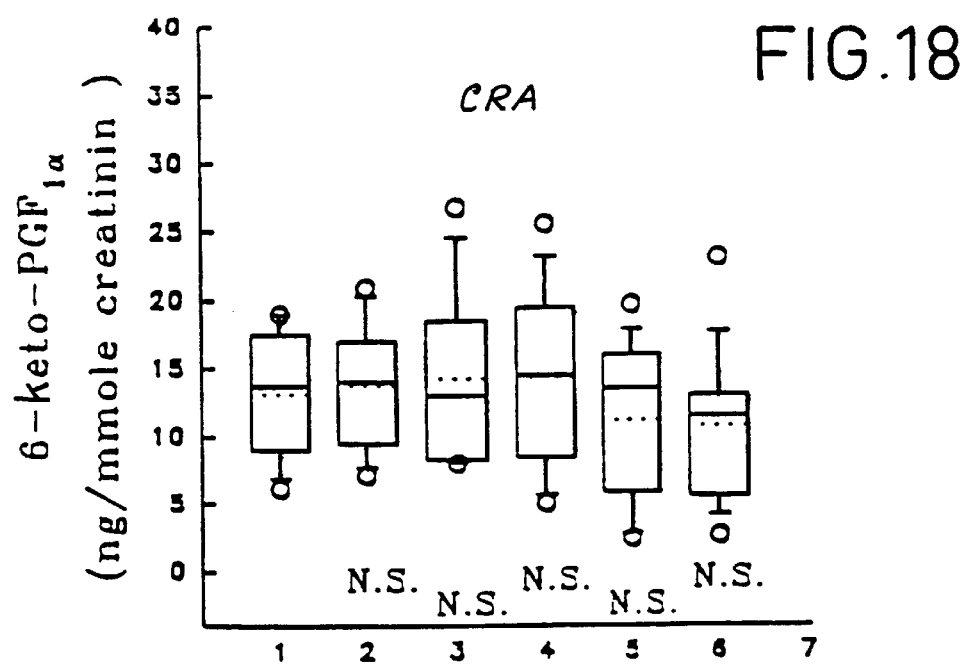

FIGS. 17 and 18 show the influence of the treatments with control ASA and CRA, respectively, on the urinary excretion of 6-ketoprostaglandin $F1\alpha$ at the times D0, D1, D14, D21, D27 and D28, corresponding to the numbers 1 to 7 on the abscissa.

Thromboxane $B_2$ and 6-ketoprostaglandin $F1\alpha$ are metabolites of thromboxane $B_2$ and prostaglandin $F1\alpha$ of renal origin.

A comparison of the results and the Figures indicated above (FIGS. 6 to 18) clearly shows that the encapsulated ASA has the same inhibitory capacity as the control ASA on the thromboxane originating from the platelets: 96.93% vs 98.15% as from the third day of treatment. The results are confirmed by measurement of the urinary metabolites (77.8% vs 75.6% and 51.9% vs 68.9%).

Conversely, the encapsulated ASA exhibits a much weaker inhibition than the control ASA on the prostacycline (8.9% vs 43.2%) and the prostaglandins of renal origin (23.8% vs 42.8% and 16.6% vs 34.6%).

Thus, even a maximum dose of 320 mg of encapsulated ASA according to the invention exhibits a pronounced bioselectivity towards the prostaglandins originating from the platelets. A dose of 80 to 320 mg, preferably 160 mg, which delivers the aspirin at a rate of 10 mg to 40 mg/hour, preferably 20 mg in the first five hours and then 2 mg to 8 mg/h in the next 19 hours, preferably 4 mg/h, causes at least 95% inhibition of the thromboxane originating from the platelets and provides more than 90% protection for the vascular prostacycline.

The invention thus described provides an optimal solution to the dilemma of aspirin and ensures optimal protection from the risk of platelet aggregation for at least 24 hours after the administration of a single daily dose.

What is claimed is:

1. A process for the preparation of microcapsules for the controlled release of acetylsalicylic acid (ASA) in the gastrointestinal environment, said microcapsules being orally ingestible in a dose (D) and comprising particles of acetylsalicylic acid with a size of between 100 and 1000 μm which are coated and designed so that, when ingested orally in a single administration of a dose D of between 75 and 320 mg of ASA, they induce moderate ASA absorption kinetics in vivo in man, extending over at least 24 hours, said ASA absorption being:

less than or equal to 10% by weight of the absorbed fraction of D at a time t after ingestion of 0.4 hour,
   less than or equal to 50% by weight of the absorbed fraction of at t=3.9 hours, and
   less than or equal to 90% by weight of the absorbed fraction of D at t=23 hours, t being given to within ±10%, which process consists essentially in:
   a) preparing a coating composition by mixing a film-forming polymer ($P_1$) insoluble in the gastrointestinal environment, a water-soluble polymer ($P_2$), a solid lubricating filler and a hydrophobic plasticizer in a solvent system,
   b) applying the composition/solvent system mixture to particles of acetylsalicylic acid, and
   c) drying the resulting microcapsules.

2. A process according to claim 1 further comprising the step of mixing the microcapsules with an anticaking agent.

3. The process according to claim 1 wherein the solvent system is formed of compounds selected from the group consisting of: ketones, esters, chlorinated solvents, alcohols, alkanes and mixtures thereof.

4. The process according to claim 3 wherein the solvent system is formed of aliphatic alcohols.

5. The process according to claim 3 wherein the solvent system is formed of $C_1$–$C_6$ compounds.

6. The process according to claim 5 wherein the solvent system is formed of $C_1$–$C_6$ compounds selected from the group consisting of acetone, methyl ethyl ketone, methyl acetate, ethyl acetate, methanol, ethanol, isopropanol and methylene chloride.

7. The process according to claim 3 wherein the solvent system is formed of a chlorinated solvent which is methylene chloride.

8. The process according to claim 1 wherein the coating composition/solvent system mixture is applied by being sprayed onto moving particles of ASA, said movement preferably being created by mechanical agitation or by blowing (fluidization).

9. The process according to claim 1 wherein step (a) comprises mixing 10 to 30 parts by weight of a film-forming polymer ($P_1$); 1 to 3 parts by weight of a plasticizer per 1 to 3 parts by weight of a water-soluble polymer ($P_2$) in solution, wherein the solvent system is selected from the group consisting of an acetone/alkanol mixture in a ratio of between 50/50 and 70/30 (v/v), cyclohexane, toluene, carbon tetrachloride, chloroform and methylene chloride; and 2 to 4 parts by weight of lubricant based on 1 to 3 parts by weight of the water-soluble polymer ($P_2$).

10. The process according to claim 9 further comprising the step of mixing the microcapsules with 0.5 to 2 parts by weight of an antiadherent, based on 1 to 3 parts by weight of the water-soluble polymer ($P_2$).

11. The process according to claim 1 wherein step (a) comprises preparing a coating composition by mixing ethyl cellulose, polyvinyl pyrrolidone, castor oil and magnesium stearate in a solvent system of a mixture of acetone and propanol; step (b) comprises applying the composition/solvent system mixture to the particles of acetylsalicylic acid via spraying in a fluidized bed; and step (c) comprises drying the microcapsules in a fluidized bed.

12. A process according to claim 1, wherein in step a) the film-forming polymer ($P_1$) is selected from the group consisting of zein, ethyl cellulose, vinyl chloride, vinyl acetate, vinyl acetate copolymers, copolymers of one or more compounds selected from the group consisting of ethyl acrylate, methyl acrylate and methacrylate, and mixtures thereof;

the water-soluble polymer ($P_2$) is selected from the group consisting of polyvinylpyrrolidone, hydroxypropyl cellulose, hydroxypropyl methyl cellulose, hydroxymethyl ethyl cellulose and methyl cellulose; vinyl acetate/crotonic acid copolymers, maleic anhydride/methyl vinyl ether copolymers, and mixtures thereof;

the solid lubricating filler is selected from the group consisting of alkaline earth metal salts of stearic acid, magnesium silicates, kaolin, talc, silica and mixtures thereof; and the hydrophobic plasticizer is selected from the group consisting of stearates of a glycol, citrates, phthalates, esters of cetyl alcohol, sebacates, tartrates, castor oil, cutin and synthetic resins.

13. A process according to claim 1 wherein in step b) the particles of acetylsalicylic acid have a size of between 250 and 800μ/m.

14. A process according to claim 1 wherein in step b) the particles of acetylsalicylic acid have a size of between 300 and 500 μm.

15. A process according to claim 2 wherein the anticaking agent is selected from the group consisting of talc, colloidal silica and a mixture of talc and silica.

16. A galenical form of aspirin containing the microcapsules produced according to the process of claim 1.

17. A galenical form according to claim 16 selected from the group consisting of tablets, powder and gelatin capsules.

18. A galenical form according to claim 16 which is presented in the form of tablets, powders or gelatin capsules containing 20 to 500 mg ASA equivalents.

19. The galenical form according to claim 18 which is administered per os in single daily doses each comprising between 50 to 400 mg of ASA equivalents.

20. The galenical form according to claim 19 which is administered per os in single daily doses each comprising between 75 to 320 mg of ASA equivalents.

21. A method of preventing and/or treating pathological disorders associated with excesses of thromboxane, particularly cardiovascular diseases and risks, which comprises oral administration of an effective amount of the galenical forms according to claim 16.

22. The method according to claim 21 which comprises oral administration of a single daily dose of between 75 and 320 mg of ASA equivalents.

23. A method for biochemically selectively inhibiting thromboxane relative to other prostaglandins, which comprises oral administration of an effective amount of the galenical form of claim 16.

24. A method for inhibiting platelet aggregation, which comprises oral administration of an effective amount of the galenical form of claim 16.

* * * * *